US00PP19996P2

(12) United States Plant Patent
Korlipara

(10) Patent No.: US PP19,996 P2
(45) Date of Patent: May 12, 2009

(54) ***VIOLA* PLANT NAMED 'HEARTTHROB'**

(50) Latin Name: *Viola*
Varietal Denomination: Heartthrob

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/156,827

(22) Filed: Jun. 3, 2008

(51) Int. Cl.
*A01H 5/00* (2006.01)

(52) U.S. Cl. ..... Plt./323

(58) Field of Classification Search ..... Plt./323
See application file for complete search history.

*Primary Examiner*—Annette H Para
(74) *Attorney, Agent, or Firm*—Klarquist Sparkman, LLP

(57) ABSTRACT

A new and distinct *Viola* plant characterized by large heart shaped leaves with a large center purple brown blotch and deep green edges, and excellent vigor.

1 Drawing Sheet

Botanical denomination: *Viola* spp.
Variety designation: 'Heartthrob'.
Parent variety: 'Mars'.

BACKGROUND OF THE INVENTION

The present invention relates to a new and distinct *Viola* spp. and given the cultivar name of 'Heartthrob'. *Viola* is in the family Violaceae. The new cultivar originated as a tissue culture mutation of *Viola* 'Mars' (an unpatented plant) in a laboratory. This mutant has proved stable since it was discovered in September of 2004.

Compared to the parent plant, *Viola* 'Mars' the new variety has larger leaves with a larger, darker blotch and a deeper, bluer green edge.

SUMMARY OF THE INVENTION

This new *Viola* is distinguished by:

1. large heart shaped leaves with a large center purple brown blotch and deep green edges, and
2. excellent vigor.

This new cultivar has been reproduced only by asexual propagation (division and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows the foliage and habit of a two-year-old *Viola* 'Heartthrob' in April in Canby, Oreg.

FIG. 2 shows the flowers in April in Canby, Oreg.

DETAILED PLANT DESCRIPTION

The following is a detailed description of the new *Viola* based on observations of two-year-old specimens grown in the ground in full shade in the trial fields in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 5 to 9.
- *Size.*—35 cm wide and 20 cm tall.
- *Form.*—Clumping.
- *Vigor.*—Excellent.
- *Stems.*—None, rosette forming.
- *Roots.*—Fibrous network, Greyed Brown 199D.

Leaf:
- *Type.*—Simple.
- *Shape.*—Ovate.
- *Arrangement.*—Basal.
- *Blade size.*—Grows to 9 cm long and 7.5 cm wide.
- *Margins.*—Crenate.
- *Apex.*—Acute to acuminate.
- *Base.*—Cordate and attenuate.
- *Petiole.*—Grows to 21 cm long and 4 mm wide, somewhat fleshy, flattened on top surface, pubescent when young, glabrous and glossy when mature, closest to Yellow Green 148B.
- *Venation.*—Palmate.
- *Surface texture.*—Glabrous on both surfaces.
- *Color.*—Topside — ¾ of the leaf center between Brown 200A and Greyed Purple 187A and Green 137A on edges; bottom side — Yellow Green 147B with dark blotch near base between Brown 200A and Greyed Purple 187A.

Inflorescence:
- *Type.*—Solitary, appear before the leaves fully expand.
- *Peduncle.*—Grows to 6.5 cm long, 2.5 mm wide, glabrous, between Greyed Green 197A and Grey Brown 199B.

Flower bud:
- *Size.*—12 mm long and 6 mm wide.
- *Shape.*—Ovoid, down facing.
- *Color.*—Violet 86B.

Flower:

*Type.*—Bisexual, zygomorphic.

*Size.*—25 mm long and 25 mm wide.

*Corolla description.*—5 separate petals, unequal, obovate, entire, obtuse, glabrous on both sides, 20 mm long and 10 mm wide; uppermost pair reflexed and erect, lateral pair spreading, lowermost spurred (10 mm long and 4 mm wide); top and bottom side colors: uppermost pair Violet 86C, lateral pair Violet 86D on top ¾, bottom ¼ White 155D, lowermost Violet 86C on top ⅔, bottom ⅓ White 155D with darker veins, Violet Blue 89C, spur between Greyed Green 197A and Violet Blue 89C.

*Calyx description.*—5 sepals, 9 mm long and 3 mm wide, entire, tip acute, glabrous and Yellow Green 147A inside and out.

*Pistil description.*—1 in number, 5 mm long and 2.3 mm wide, ovary 2 mm long and 2.3 mm wide, Yellow Green 148A; stigma and style 3 mm long, Yellow Green 145D.

*Stamen description.*—5 in number, 3.5 mm long, filaments 2 mm long, flattened, Yellow Green 147D on the inside and Violet 86A on the back; anthers 1.5 mm long, Yellow Orange 23A; pollen not seen.

*Bloom period.*—March to April in Canby, Oreg.

*Lastingness of bloom.*—Each flower lasts about a week.

*Fragrance.*—None.

Fruit: A 3 chambered capsule, Yellow Green 147A.

Seed: Little produced, 1 mm round, Black 202A.

Pest and diseases: *Viola* are troubled by aphids, snails and slugs. This variety has no known resistances.

I claim:

1. A new and distinct *Viola* plant as herein illustrated and described.

* * * * *

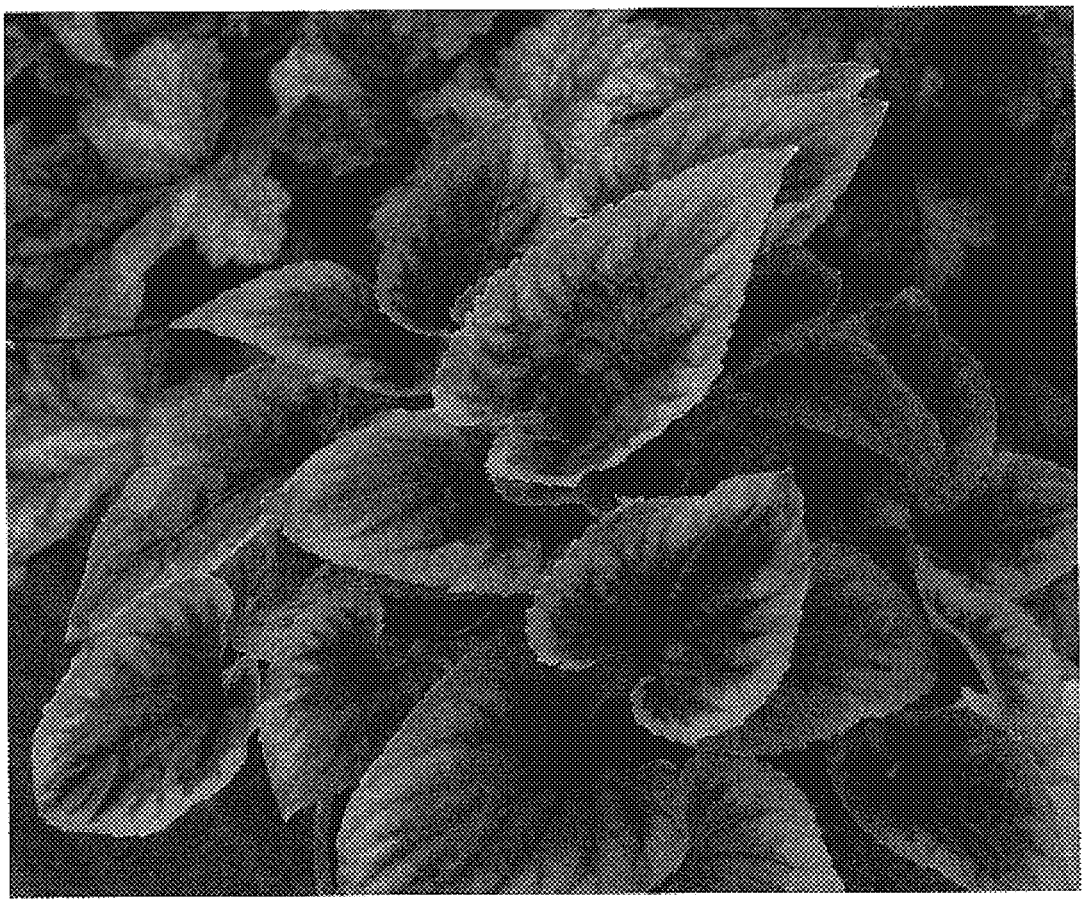

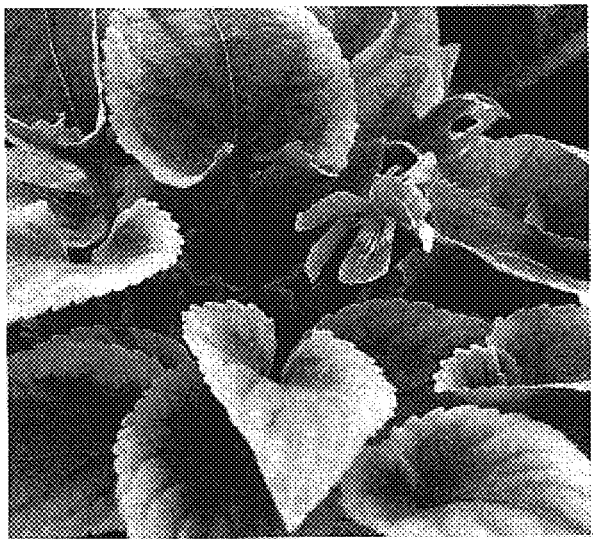
Figure 1 above, Figure 2 below